US008883227B2

(12) United States Patent
Su et al.

(10) Patent No.: US 8,883,227 B2
(45) Date of Patent: *Nov. 11, 2014

(54) PLANT PATHOGEN INHIBITOR COMBINATIONS AND METHODS OF USE

(71) Applicant: Marrone Bio Innovations, Inc., Davis, CA (US)

(72) Inventors: Hai Su, Davis, CA (US); Marja Koivunen, Davis, CA (US); Pamela Marrone, Davis, CA (US)

(73) Assignee: Marrone Bio Innovations, Inc., Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/081,350

(22) Filed: Nov. 15, 2013

(65) Prior Publication Data

US 2014/0073675 A1 Mar. 13, 2014

Related U.S. Application Data

(63) Continuation of application No. 12/845,883, filed on Jul. 29, 2010.

(60) Provisional application No. 61/230,102, filed on Jul. 30, 2009.

(51) Int. Cl.
*A61K 36/00* (2006.01)
*A61K 35/00* (2006.01)
*A61K 31/41* (2006.01)
*A01N 65/00* (2009.01)
*A01N 43/82* (2006.01)
*A01N 45/02* (2006.01)

(52) U.S. Cl.
CPC ............... *A01N 45/02* (2013.01); *A01N 65/00* (2013.01); *A01N 43/82* (2013.01)
USPC ........................... 424/725; 424/780; 514/361

(58) Field of Classification Search
None
See application file for complete search history.

(56) References Cited

U.S. PATENT DOCUMENTS

| 3,726,850 | A | 4/1973 | Detroit et al. |
|---|---|---|---|
| 3,813,236 | A | 5/1974 | Allan et al. |
| 3,929,453 | A | 12/1975 | Dimitri et al. |
| 4,381,194 | A | 4/1983 | DelliColli et al. |
| 4,602,004 | A | 7/1986 | Cohen |
| 4,612,051 | A | 9/1986 | Miller et al. |
| 4,666,522 | A | 5/1987 | Hollis et al. |
| 4,863,734 | A | 9/1989 | Pommer et al. |
| 5,300,521 | A | 4/1994 | Eberle et al. |
| 5,668,183 | A | 9/1997 | Leuenberger |
| 5,885,604 | A | 3/1999 | Ballinger |
| 5,989,429 | A | 11/1999 | Bardinelli et al. |
| 5,994,266 | A | 11/1999 | Hobbs et al. |
| 6,172,004 | B1 | 1/2001 | Brinker et al. |
| 7,344,730 | B1 | 3/2008 | Stadler et al. |
| 7,867,507 | B2 | 1/2011 | Birthisel et al. |
| 2003/0012804 | A1 | 1/2003 | Cutler et al. |
| 2004/0096428 | A1 | 5/2004 | Jijakli et al. |
| 2005/0163815 | A1 | 7/2005 | Bowen et al. |
| 2006/0247130 | A1 | 11/2006 | Van der Krieken et al. |
| 2007/0191292 | A1 | 8/2007 | Gandhi et al. |
| 2007/0264363 | A1 | 11/2007 | Bowen et al. |
| 2008/0113920 | A1 | 5/2008 | Yang et al. |
| 2008/0193387 | A1 | 8/2008 | De Wolff et al. |
| 2009/0246293 | A1 | 10/2009 | Ehr et al. |
| 2010/0136132 | A1 | 6/2010 | Van der Krieken et al. |
| 2010/0154498 | A1 | 6/2010 | Valencia |
| 2010/0278890 | A1 | 11/2010 | Winowiski |
| 2011/0015237 | A1 | 1/2011 | Morita et al. |
| 2011/0082215 | A1 | 4/2011 | Huang et al. |
| 2012/0115728 | A1 | 5/2012 | Su et al. |
| 2012/0196751 | A1 | 8/2012 | Namnath et al. |

FOREIGN PATENT DOCUMENTS

| DE | 4411895 | 5/1995 |
|---|---|---|
| EP | 0173410 | 3/1986 |
| JP | H0899813 | 4/1996 |
| JP | H08109112 | 4/1996 |
| JP | 2000-033383 | 2/2000 |
| JP | 2000-034202 | 2/2000 |
| WO | WO 98/11782 A1 | 3/1998 |
| WO | WO 03005816 | 1/2003 |
| WO | WO 04000014 | 12/2003 |
| WO | WO 2005010315 | 2/2005 |
| WO | WO 2006015865 | 2/2006 |
| WO | WO 2006037632 | 4/2006 |
| WO | WO 2006037633 | 4/2006 |
| WO | WO 2006037634 | 4/2006 |
| WO | WO 2010040834 | 4/2010 |

OTHER PUBLICATIONS

Agarwal, S. et al., "Antifungal Activity of Anthraquinone Derivatives from *Rheum emodi*," *J. Ethnopharmacol.* 72:43-46 (2000).
Bardin, M. et al., "Compatibility Between Biopesticides Used to Control Grey Mould, Powdery Mildew and Whitefly on Tomato," *Biological Control* 46:476-483 (2008).
Bartlett, D.W. et al., "The Strobilurin Fungicides," *Pest Management Science* 58:649-662 (2002).
Belanger, R.R. et al., "Challenges and Prospects for Integrated Control of Powdery Mildews in the Greenhouse," *Can. J. Plant Pathol.* 19:310-314 (1997).
Bokshi, A.I. et al., "A Single Application of Milsana® Followed by Bion® Assists in the Control of Powdery Mildew in Cucumber and Helps Overcome Yield Losses," *J. Horticltural Science & Biotechnology* 83:701-706 (2008).
Braun, U. et al., "The Taxonomy of the Powdery Mildew Fungi," In *The Powdery Mildews: A Comprehensive Treatise.* R.R. Belanger et al. eds. APS Press, St. Paul, MN, pp. 13-55.
Bravo Fungicide draft, 10-1000L Draft Label Text. Container (Apr. 2009).

(Continued)

*Primary Examiner* — Chris R Tate
*Assistant Examiner* — Russell Fiebig
(74) *Attorney, Agent, or Firm* — Ying-Horng Liu

(57) ABSTRACT

Combinations, compositions and methods of use for modulating plant pathogen infection using plant extracts containing anthraquinone derivatives which induce resistance to plant phytopathogens and an antimicrobial agent, a biological control agent and/or a surfactant having fungicidal activity.

9 Claims, No Drawings

(56) References Cited

OTHER PUBLICATIONS

Burpee, L. et al., "Reassessment of Fungicide Synergism for Control of Dollar Spot," *Plant Disease* 92:601-606 (2008).
Captan, General Fact Sheet. National Pesticide Information Center (2002).
Daayf, F. et al., "The Effects of Plant Extracts of *Reynoutria sachalinensis* on Powdery Mildew Development and Leaf Physiology of Long English Cucumber," *Plant Disease* 79:577-580 (1995).
De Waard, M.A., "Synergism and Antagonism in Fungicide Mixtures Containing Sterol Demethylation Inhibitors," *Phytopathology* 86:1280-1283 (1996).
Dow AgroSciences Nova™ 40W Agricultural Fungicide, Material Safety Data Sheet (Mar. 2009).
Durrant, W.E. et al., "Systemic Acquired Resistance," *Annu. Rev. Phytopathol.* 42:185-209 (2004).
Fraaije, B.A. et al., "QoI Resistance Development in Populations of Cereal Pathogens in the UK," *Crop Science & Technology* pp. 689-694 (2003).
Fofana, B. et al., "Milsana-Induced Resistance in Powdery Mildew-Infected Cucumber Plants Correlates With the Induction of Chalcone Synthase and Chalcone Isomerase," *Physiol. Molec. Plant Pathol.* 61:121-132 (2002).
Fongicide Elevate® 50 WDG, Arysta LifeScience North America LLC, (Aug. 2007) (French language document).
Gisi, U., "Synergistic Interaction of Fungicides in Mixtures," *Phytopathology* 86:1273-1279 (1996).
Hafez, M.B. et al., "The Side-Effects of Plant Extracts and Metabolites of *Reynoutria sachalinensis* (F. Schmidt) Nakai and Conventional Fungicides on the Beneficial Organism *Trichogramma cacoeciae* Marchal (Hym., Trichogrammatidae)," *J. Appl. Ent.* 123:363-368 (1999).
Holb, I.J. et al., "The Benefits of Combining Elemental Sulfur with a DMI Fungicide to Control *Monilinia fructicola* Isolates Resistant to Propiconazole," *Pest Management Science* 64:156-164 (2008).
Horst, R.K. et al., "Effect of Sodium Bicarbonate and Oils on the Control of Powdery Mildew and Black Spot of Roses," *Plant Disease* 76:247-251 (1992).
Hwang, S-F. et al., "Effect of Seed Treatments and Root Pathogens on Seedling Establishment and Yield of Alfalfa, Birdsfoot Trefoil and Sweetclover," *Plant Pathology Journal* 5:322-328 (2006).
Izhaki, I., "Emodin—A Secondary Metabolite with Multiple Ecological Functions in Higher Plants," *New Phytologist* 155:205-217 (2002).
James, C., "A Manual of Assessment Keys for Plant Diseases," Canada Department of Agriculture Publication No. 1458 1971, Key Nos. 2.2 and 2.4. American Phytopathological Society, St. Paul, MN. (1971).
Karaoglanidis, G.S. et al., "Efficacy of Strobilurins and Mixtures with DMI Fungicides in Controlling Powdery Mildew in Field-Grown Sugar Beet," *Crop Protection* 25:977-983 (2006).
Keinath, A.P., et al., "Use of Biofungicides and Reduced-Risk Fungicides Rotated With Chlorothalonil to Control Downy Mildew on Muskmelon, 2002," *F&N Tests Report* No. 58:V024 (2002).
Keinath, A.P. et al., "Reduced-Risk Fungicides Rotated or Mixed with Chlorothalonil to Manage Downy Mildew on Muskmelon, 2003," *F&N Tests Report* No. 59:V004 (2003).
Kong, L.D., et al., "Inhibition of MAO A and B by Some Plant-Derived Alkaloids, Phenols and Anthraquinones," *J. Ethnopharmacology* 91:351-355 (2004).
Konstantinidou-Doltsinis, S. et al., "Control of Powdery Mildew of Grape in Greece Using Sporodex® L and Milsana®," *J. Plant Dis. Protect.* 114:256-262 (2007).
Krishnakumari, G.N., et al., "Antifeedant Activity of Quinones from Ventilago Madaraspatana," *Fitoterapia* 72:671-675 (2001).
Kuc, J., "Development and Future Direction of Induced Systemic Resistance in Plants," *Crop Protection* 19:859-861 (2000).
Langston, D.B., et al., "Control of Alternaria Leaf Spot of Muskmelon with Biofungicides and Reduced-Risk Fungicides Alternated with Chrlothalonil, 2002," *F&N Tests Report* No. 58:V082 (2002).
Langston, D.B., "Rotation of Biocides with Powdery Mildew Fungicides to Suppress Powdery Mildew of Squash in Georgia, 2003," *F&N Tests Report* No. 59:V135 (2003).
Langston, D.B., "Evaluation of Fungicides and Spray Programs for Control of Powdery Mildew in Summer Squash in Georgia II, 2004," *F&N Tests Report* No. 60:V137 (2004).
Lehnhof, F., "Milsana® A *Reynoutria sachalinensis* Based Plant Extract for Preventive Control of Powdery Mildew," BIOFA; http://www.abim.ch/fileadmin/documents-abim/presentations2007/session5/1_lehnhof_abim_2007.pdf (2007).
Limpel, L.E. et al., "Weed Control by Dimethyl Tetrachloroterephthalate Alone and in Certain Combinations," *N.E. Weed Control Conference* 16:48-53 (1962).
Liu, S.Y., et al., "Anthraquinones in *Rheum palmatum* and *Rumex dentatus* (Polygonaceae), and Phorbol Esteres in *Jatropha curcas* (Euphorbiaceae) with Molluscicidal Activity Against the Schistosome Vector Snails *Oncomelania, Biomphalaria* and *Bulinus*," *Tropical Medicine and International Health,* 2:179-188 (1997).
Matheron, M.E., et al., "Evaluation of Fungicides for Management of Powdery Mildew on Lettuce, 2003," *F&N Tests Report* No. 59:V089 (2003).
May, R.M., "Evolution of Pesticide Resistance," *Nature* 315:12-13 (1985).
McGrath, M.T., et al., "Evaluation of Fungicide Programs for Managing Powdery Mildew of Pumpkin, 2000," *F&N Tests Report* No. 56:V76 (2000).
McGrath, M.T., "Evaluation of Fungicide Programs for Managing Powdery Mildew of Pumpkin, 2001," *F&N Tests Report* No. 57:V086 (2001).
McGrath, M.T., "Fungicide Resistance in Cucurbit Powdery Mildew: Experiences and Challenges," *Plant Disease* 85:236-245 (2001).
McGrath, M.T., "Occurrence of Strobilurin Resistance and Impact on Managing Powdery Mildew of Cucurbits," *Cornell University Vegetable MD Online* (2003).
McGrath, M.T., "Guidelines for Managing Cucurbit Powdery Mildew in 2006," *Cornell University Vegetable MD Online* (2006).
Muravieva, D.A., "Pharmacognosy," Medicine Publishing House, Moscow, pp. 494-529 (1978).
Nash, R.G., "Phytotoxic Interaction Studies—Techniques for Evaluation and Presentation of Results," *Weed Science* 29:147-155 (1981).
Penncozeb® 80 WP Fungicide. Group M Fungicide—label and booklet (2008) (Pest Management Regulatory Agency label transcript service).
Pesticide Alert, Strawberry News Bulletin—Cabrio Registered for Use on Strawberries (Feb. 24, 2003) (English and Spanish).
Randoux, B., et al., "Inhibition of *Blumeria graminis* f. sp. *tritici* Germination and Partial Enhancement of Wheat Defenses by Milsana," *Phytopathology* 96:1278-1286 (2006).
Regalia® Bioprotectant Concentrate Label (May 2009).
Regalia® SC A Powerful New Tool for Powdery Mildew and Gummy Stem Blight on Cucurbits Fact Sheet 1 (May 2009).
Regalia® SC A Powerful New Tool for Powdery Mildew Control on Cucurbits Fact Sheet 2 (May 2009).
Reuveni, M., "Improved Control of Powdery Mildew (*Sphaerotheca pannosa*) of Nectarines in Israel Using Strobilurin and Polyoxin B Fungicides; Mixtures with Sulfur; and Early Bloom Applications," *Crop Protection* 20:663-668 (2001).
Richer, D.L., "Synergism—a Patent View," *Pesticide Science* 19:309-315 (1987).
Rosenberger, D.A., et al., "Controlling Diseases on Jerseymac and Ginger Gold Apples with Biocontrol and Contact Fungicides, 1999," *F&N Tests Report* No. 55:25 (1999).
Ross, A.F., "Systemic Acquired Resistance Induced by Localized Virus Infections in Plants," *Virology* 14:340-358 (1961).
Samoucha, Y. et al., "Synergy Between Metalaxyl and Mancozeb in Controlling Downy Mildew in Cucumbers," *Phytopathology* 74:1434-1437 (1984).
Schilder, A.M.C., et al., "Evaluation of Fungicides for Control of Foliar Diseases of Strawberries, 2003," *F&N Tests Report* No. 59:SMF029 (2003).
Schmitt, A., "Induced Responses by Plant Extracts From *Reynoutria sachalinensis:* A Case Study," *Induced Resistance in Plants against Insects and Diseases IOBC/wprs Bull.* 25:83-88 (2002).

(56) References Cited

OTHER PUBLICATIONS

Schmitt, A., "Biocontrol of Plant Pathogens with Microbial BCAs and Plant Extracts—Advantages of Single and Combined Use," *Modern Fungicides and Antifungal Compounds IV: Proceedings of the 14th International Reinhardsbrunn Symposium* 2004, Alton, UK pp. 205-225 (2005) (Abstract only).
Schmitt, A. et al., "Use of *Reynoutria sachalinensis* Plant Extracts, Clay Preparations and *Brevibacillus brevis* Against Fungal Diseases of Grape Berries," *10th International Conference on Cultivation Technique and Phytopathological Problems in Organic Fruit-Growing and Viticulture,* Weinsberg, Germany7, pp. 146-151 (2002).
Schnabel, G. et al., "Reduced Sensitivity in *Monilinia fructicola* to Propiconazole in Georgia and Implications for Disease Management," *Plant Dis.* 88:1000-1004 (2004).
Singh, D.N., et al., "Antifungal Anthraquinones from *Saprosma fragrans,*" *Bioorganic & Medicinal Chemistry Letters* 16:4512-4514 (2006).
Stromberg, E.L., "Evaluation of Foliar Fungicides and a Botanical for Disease Control in FFR 555 Soft Red Winter Wheat in Virginia, 1999," *F&N Tests Report* No. 55:353 (1999).
Su, H. et al., "Sporulation of *Bremia lactucae* Affected by Temperature, Relative Humidity, and Wind in Controlled Conditions," *Phytopathology* 94:396-401 (2004).
Tamokou, J.D.D., et al., "Antimicrobial Activities of Methanol Extract and Compounds From Stem Bark of *Vismia rubescens," J. Ethnopharmacology,* 124:571-575 (2009).
Tiebre, M-S., et al., "Hybridization and Sexual Reproduction in the Invasive Alien *Fallopia* (Polygonaceae) Complex in Belgium," *Annals of Botany,* 99:193-203 (2007).
Van Den Bosch, F. et al., "Models of Fungicide Resistance Dynamics," *Annu. Rev. Phytopathol.* 46:123-147 (2008).
Van Loon, L.C. et al., "Systemic Resistance Induced by Rhizosphere Bacteria," *Annu. Rev. Phytopathol.* 36:453-483 (1998).
Vechet, L. et al., "A Comparative Study of the Efficacy of Several Sources of Induced Resistance to Powdery Mildew (*Blumeria graminis* f. sp. *tritici*) in Wheat Under Field Conditions," *Crop Protection* 28:151-154 (2009).
Verma, S.C., et al., "Determination and Locational Variations in the Quantity of Hydroxyanthraquinones and Their Glycosides in Rhizomes of *Rheum emodi* Using High-Performance Liquid Chromatography," *J. Chromatography A* 1097:59-65 (2005).
Vrchotova, N., et al., "The Stilbene and Catechin Content of the Spring Sprouts of *Reynoutria* Species," *Acta Chromatographica* 19:21-28 (2007).
Walters, D. et al., "Induced Resistance for Plant Disease Control: Maximizing the Efficacy of Resistance Elicitors," *Phytopathology* 95:1368-1373 (2005).
Werner, S.J., et al., "Anthraquinone-Based Bird Repellent for Sunflower Crops," *Applied Animal Behaviour Science,* 129:162-169 (2011).
Wurms, K. et al., "Effects of Milsana and Benzothiadiazole on the Ultrastructure of Powdery Mildew Haustoria on Cucumber," *Phytopathology* 89:728-736 (1999).
Wyenandt, C.A. et al., "Fungicide Resistance Management Guidelines for Cucurbit Downy and Powdery Mildew Control in the Mid-Atlantic and Northeast Regions of the U.S.," *Phytopathology* 99:S144 (2009).
Yang, X, et al., "Synergistic Interaction of Physcion and Chrysophanol on Plant Powdery Mildew," *Pest Management Science* 63:511-515 (2007).
Examination Report in New Zealand Patent App. No. 598365, dated Sep. 17, 2012.
Examination Report in New Zealand Patent App. No. 599664, dated Nov. 29, 2012.
International Preliminary Report on Patentability in PCT App. No. PCT/US2010/043612, dated Feb. 9, 2012.
International Preliminary Report on Patentability in PCT App. No. PCT/US2010/051359, dated Apr. 19, 2012.
International Search Report and Written Opinion in PCT App. No. PCT/US2010/051359, dated Jun. 24, 2011.
International Search Report and Written Opinion in PCT App. No. PCT/US2010/043612, dated Aug. 2, 2011.
International Search Report and Written Opinion in PCT App. No. PCT/US2010/043612, dated Jul. 29, 2010.
International Search Report in PCT App. No. PCT/US12/23571, dated May 24, 2012.
International Search Report in PCT App. No. PCT/US2011/059197, dated Jun. 29, 2012.
International Search Report and Invitation to Pay Fees for Additional Search in PCT App. No. PCT/US2010/043612, dated May 2, 2011.
Office Action in U.S. Appl. No. 12/897,776, dated Aug. 2, 2012.
Third Party Observations in EP Patent App. No. 10805012.1.
Supplementary European Search Report in EP App. No. 10805012.1 dated Dec. 13, 2013, 11 pages.

PLANT PATHOGEN INHIBITOR COMBINATIONS AND METHODS OF USE

CROSS REFERENCE TO RELATED APPLICATIONS

This application is a continuation application of U.S. application Ser. No. 12/845,883, filed Jul. 29, 2010, which claims the benefit under 35 U.S.C. §119(e) of U.S. Provisional Application No. 61/230,102, filed Jul. 30, 2009, both of which are hereby incorporated by reference into the present disclosure.

TECHNICAL FIELD

Disclosed herein are combinations, compositions and methods of use for modulating plant pathogen infection using plant extracts containing anthraquinone derivatives which induce resistance to plant phytopathogens and an antimicrobial agent, a biological control agent and/or a surfactant having fungicidal activity.

BACKGROUND

Plant Resistance to Plant Pathogens

Plants have evolved highly effective mechanisms for resistance to disease caused by infectious agents, such as bacteria, fungi and viruses. This resistance can be caused by several mechanisms, the best known of which are the systemic acquired resistance (SAR; Ross, 1961; Durrant and Dong, 2004) and induced systemic resistance (ISR; van Loon et al., 1998). In the most simple case, the inducer is the plant pathogen itself, in other cases, the inducer can be either a chemical compound (salicylic acid, benzo(1,2,3)thiadiazole-7-carbothioic acid S-methyl ester also known as BTH) or physical impact such as water or heat stress (Walters et al., 2005). It appears that induced systemic resistance depends upon a gradual expression and persistence of a low level of metabolic perturbation. Unlike elicitors of phytoalexin accumulation, which elicit at the site of application and may be responsible for localized protection, inducers of systemic resistance sensitize the plant as a whole to respond rapidly after infections. These responses include phytoalexin accumulation, lignification and enhanced activities of chitinase and glucanase.

Extract from giant knotweed (*Reynoutria sachalinensis*) sold as MILSANA® and REGALIA® by Marrone Bio Innovations, Inc.) provides control of powdery mildew and other plant diseases on cucurbits and other crops mainly by inducing an accumulation of fungitoxic phenolic compounds in the plant (Daayf et al., 1995; Wurms et al. 1999; Schmitt, 2002). Recently, formulated giant knotweed extract has also shown great efficiency in inducing resistance in various crops and plant pathogens including wheat powdery mildew (Vechet et al., 2009). Besides the ISR mode of action, the formulated *R. sachalinensis* extract has recently also been shown to have a direct fungistatic effect against wheat powdery mildew (*Blumeria graminis* f. sp. *tritici*; Randoux et al., 2008).

Fungicide Resistance

Fungicide resistance is a common phenomenon in pests including plant pathogens. When a fungicide, especially those with single-site mode of action, is frequently used, the targeted pathogen can adapt to the fungicide due to high selection pressure. It is estimated that pests can develop resistance to pesticides within 5-50 generations (May, 1985). Most plant pathogens fit in this range in one growth season and thus can develop fungicide resistance quickly. For example, it only took one year for benomyl lost efficacy for control of cucurbit powdery mildew after its first registration for commercial use (McGrath, 2001).

Quinone outside inhibitors (also known as QoI fungicides or strobilurins) has been widely used to control agriculturally important fungal pathogens since their introduction in 1996. Strobilurins block the respiration pathway by inhibiting the cytochrome bc1 complex in mitochondria, thereby blocking the electron transfer process in the respiration chain and causing an energy deficiency due to lack of adenosine triphosphate (ATP) (Bartlett et al., 2002). Strobilurins and other fungicides with a single-site mode of action such as demethylation inhibitors (DMI) are prone to resistance development among plant pathogens. To date, several plant pathogenic fungi have developed field resistance to strobilurins (Tuttle McGrath, 2003; Fraaije et al., 2003) and DMI fungicides (Schnabel et al., 2004), and considerable effort has been made worldwide to develop appropriate resistance management strategies with detailed recommendations of how to combine fungicides and other antifungal compounds in programs and rotations to minimize the risk of resistance development (Tuttle McGrath, 2006; Wyenandt et al., 2009).

Methods to Control Fungicide Resistance

The most common strategy to manage fungicide resistance is to use site-specific fungicides that are prone to resistance development in a combination (pre-mix or tank mix). Besides resistance management, tank mixes also offer a compensatory mechanism in case of a failure of one fungicide as well as a way to reduce the dose to reduce selection pressure on pathogens (van den Bosch and Gilligan, 2008). In some cases, the combination of single and multisite fungicides in a tank mix or in rotation can provide additive or even synergistic interactions (Gisi, 1996). Holb and Schnabel (2008) were able to show improved control of brown rot (*Monilinia fructicola*) in a field study with a tank mix of a DMI fungicide and elemental sulfur, and Reuveni (2001) demonstrated the benefits of using strobilurins and polyoxin B fungicides in combination with sulfur to control powdery mildew in nectarines.

Plant defense inducers such as the extract of *R. sachalinensis* have been tested in tank mixes and rotations with other SAR/ISR products as well as with biocontrol agents (BCA) (Hafez et al., 1999; Belanger and Benyagoub, 1997; Schmitt et al., 2002; Schmitt and Seddon, 2005; Bardin et al., 2008). The purpose of these studies has mainly been to demonstrate the compatibility of different types of plant extracts with biocontrol agents. Konstatinidou-Doltsinis et al. (2007) tested the *R. sachalinensis* product in a rotation with *Pseudozyma flocculosa* product against powdery mildew on grapes, and found that alternated application of both products improved the efficacy of *R. sachalinensis*. In the same study, alternation of sulfur and *R. sachalinensis* in a rotation did not have a beneficial effect. Belanger and Benyagoub (1997) found that a yeast-like fungus, *Pseudozyma flocculosa*, was compatible with *R. sachalinensis* when used against cucumber powdery mildew in a greenhouse. Similarly, Bokshi et al. (2008) evaluated the combined effect of an acquired systemic resistance activator benzothiadiazole and MILSANA® against cucumber powdery mildew, and found that MILSANA® used in a rotation with benzothiadiazole provided an effective control measure against powdery mildew in the field. However, based on the disease severity and yield data collected, it was not possible to determine whether the positive effect was additive or synergistic.

Pesticide synergism has been defined as "the simultaneous action of two or more compounds in which the total response of an organism to the pesticide combination is greater than the sum of the individual components" (Nash, 1981). Hence, when fungicides interact synergistically, a high level of disease control is achieved with less than label rates of each individual fungicide. Usually, the best effect is achieved with combinations of fungicides with different modes of action (MOA), but synergy has also been demonstrated in combined use of products with similar mode of action (De Waard, 1996). Fungicide synergism has been demonstrated mostly in laboratory studies (Samoucha and Cohen, 1984; Gisi, 1996) but in some cases (Karaogladinis and Karadimos, 2006; Burpee and Latin, 2008) synergism has also been found in the field studies. Additionally, synergism of antifungal compounds other than fungicides (bicarbonates and refined petroleum distillate) has been demonstrated against rose powdery mildew and black spot (Horst et al., 1992).

SUMMARY

Disclosed and claimed is a combination comprising: (a) an extract derived from a plant, wherein said extract contains one or more anthraquinone derivatives which induce plant resistance to phytopathogens (also referred to as "plant pathogens") and (b) one or more anti-phytopathogenic agents selected from the group consisting of: (i) a non-benzodiathiazole, non-Vitamin E, non-organophosphorusanti-microbial agent, which lacks or in other words does not contain nonelemental, non-wettable sulfur, (ii) a surfactant having fungicidal activity and (iii) a non-*Bacillus*, non-*Pseudomonas*, non-*Brevabacillus*, non-*Lecanicillium*, non-*Ampelomyces*, non-*Phoma*, non-*Pseudozyma* biological control agent (e.g., an agent derived from *Streptomyces* sp., *Burkholderia* sp., *Trichoderma* sp., *Gliocladium* sp. or a natural oil or oil-product having fungicidal and/or insecticidal activity).

In a specific embodiment, the combination comprises: (a) an extract derived from the family Polygonaceae and (b) a non-benzodiathiazole, non-Vitamin E, non-organophosphorus anti-fungal and/or antibacterial agent, which lacks or does not contain non-elemental or non-wettable sulfur.

In one specific embodiment, the combination comprises (a) an extract derived from the family Polygonaceae (e.g. *Reynoutria sachalinensis*) and (b) a single site fungicide and/or multi-site fungicide which may include but is not limited to myclobutanil, quinoxyfen, azoxystrobin, acibenzolar-S-methyl, mefenoxam, triflumizole, fludioxonil, propiconazole.

In another specific embodiment, the combination comprises (a) an extract derived from the family Polygonaceae (e.g. *Reynoutria sachalinensis*) and (b) a natural oil or oil-product having fungicidal and/or insecticidal activity.

In yet another particular embodiment, the combinations are compositions, particularly compositions for use in modulating phytopathogenic or fungal infection. The invention is further directed to the use of the extract and anti-phytopathogenic agents in formulating these compositions.

The invention is additionally directed to a synergistic combination for use in modulating phytopathogenic infection comprising (a) an extract derived from a plant, wherein said plant contains anthraquinone derivatives that induce plant resistance to phytopathogens and (b) a non-Vitamin E, non-organophosphorus antimicrobial agent (e.g., anti-fungal and/or antibacterial agent), which lacks or does not contain non-elemental or non-wettable sulfur. In a particular embodiment, the antimicrobial agent is a benzodiathiazole (e.g., acibenzolar-S-methyl), a triazole (e.g., propiconazole) or a strobilurin (e.g., azoxystrobin).

The above mentioned combinations may also be formulated into compositions.

The invention is further directed to a method for modulating phytopathogenic infection in a plant comprising applying to the plant and/or seeds thereof and/or substrate used for growing said plant an amount of the combinations of the present invention set forth above effective to modulate said phytopathogenic infection.

In a particular embodiment, the invention is directed to a method for modulating fungal and/or bacterial infection in a plant comprising applying to the plant and/or seeds thereof and/or substrate used for growing said plant an amount of the combinations of the present invention effective to modulate said fungal and/or bacterial infection.

The extract and said anti-phytopathogenic agents (e.g., anti-fungal and/or antibacterial agents) may be administered sequentially, concurrently or in combination intermittently. As defined herein "phytopathogenic infection" means infection of a plant by plant pathogenic bacteria, fungi, insects, nematodes and/or mollusks.

The invention is further directed to a method for decreasing the resistance of a phytopathogen (e.g, fungus and/or bacteria) to (i) a non-Vitamin E, non-organophosphorus anti-microbial agent, which lacked or in other words did not contain non-elemental or non-wettable sulfur, (ii) a surfactant having fungicidal activity and/or (iii) a non-*Bacillus*, non-*Pseudomonas*, non-*Brevabacillus*, non-*Lecanicillium*, non-*Ampelomyces*, non-*Phoma*, non-*Pseudozyma* biological control agent (e.g., an agent derived from *Streptomyces* sp., *Burkholderia* sp., *Trichoderma* sp., *Gliocladium* sp. or a natural oil or oil-based product having fungicidal and/or insecticidal activity) comprising applying to a plant in need thereof an amount of the combinations of the present invention effective to decrease the emergence of said resistance. In a particular embodiment, the invention is directed to a method for decreasing the resistance of a fungus and/or bacteria to a non-elemental or non-wettable, sulfur, non-benzodiathiazole, non-Vitamin E, non-organophosphorus anti-fungal and/or antibacterial agent. In yet another particular embodiment, the invention is directed to a method for decreasing resistance of a fungus and/or bacteria to a natural oil or oil-based product having fungicidal and/or insecticidal activity using the combination of the present invention. This may be accomplished by decreasing the frequency or rate of emergence. The resistance of a phytopathogen to the above-mentioned anti-pathogenic agents may be reduced by at least 50%.

The invention is further directed to the use of (a) an extract derived from a plant, wherein said extract contains anthraquinone derivatives which induce plant resistance to phytopathogens, and (b) one or more anti-phytopathogenic agents selected from the group consisting of: (i) a non-benzodiathiazole, non-Vitamin E, non-organophosphorus antimicrobial agent which lacks nonelemental, non-wettable sulfur, (ii) a surfactant having fungicidal activity and (iv) a non-*Bacillus*, non-*Pseudomonas*, non-*Brevabacillus*, non-*Lecanicillium*, non-*Ampelomyces*, non-*Phoma*, non-*Pseudozyma* biological control agent for the manufacture of a composition for modulating phytopathogenic infection as well as the use of (a) an extract derived from a plant, wherein said plant contains anthraquinone derivatives that induce plant resistance to phytopathogens and (b) a benzodiathiazole anti-microbial agent for the manufacture of a synergistic composition for modulating phytopathogenic infection.

The invention is further directed to a kit comprising (a) an extract derived from the family Polygonaceae and (b) one or more anti-phytopathogenic agents selected from the group consisting of: (i) a non-benzodiathiazole, non-Vitamin E, non-organophosphorus, anti-microbial agent, which lacks a non-elemental or non-wettable sulfur, (ii) a surfactant having fungicidal activity and (iii) a non-*Bacillus*, non-*Pseudomonas*, non-*Brevabacillus*, non-*Lecanicillium*, non-*Ampelomy-* ces, non-*Phoma*, non-*Pseudozyma* biological control agent. This kit may further comprise packaging instructions.

DETAILED DESCRIPTION OF SPECIFIC EMBODIMENTS

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. Further, although this invention has been described with reference to specific embodiments, the details thereof are not to be construed as limiting, as it is obvious that one can use various equivalents, changes and modifications and still are within the scope of the present invention.

Various references are cited throughout this specification, each of which is incorporated herein by reference in its entirety.

It must be noted that as used herein and in the appended claims, the singular forms "a," "and" and "the" include plural references unless the context clearly dictates otherwise. For example, "a plant" also encompasses "plants".

As defined herein, the term "treating" means applying a particular substance to a plant to, for example, activate a plant, promote plant growth, or modulate transpiration in a plant.

As defined herein a "plant" in includes but is not limited to leaves, stem, phylloplane, roots, seeds and/or fruit of a plant.

As defined herein, the term "modulate" is used to mean to alter the amount of transpiration of a plant or rate of transpiration of a plant.

DETAILED DESCRIPTION OF THE DISCLOSURE

Extracts

The plant extracts used in the combinations, compositions and methods of the present invention contain anthraquinone derivatives as biochemical agricultural products for use against plant pests, particularly plant phytopathogens such as plant pathogenic bacteria, fungi, insects, nematodes and/or as a molluscicide. "Contain" also encompasses extracts that produce said anthraquinone derivatives. In a particular embodiment, the anthraquinone derivative(s) of the present invention which is used in compositions and methods of the present invention is (are) the major active ingredients or one of the major active ingredients.

Anthraquinone derivatives include but are not limited to physcion, emodin, chrysophanol, ventiloquinone, emodin glycoside, chrysophanol glycoside, physcion glycoside, 3,4-dihydroxy-1-methoxy anthraquinone-2-corboxaldehyde, damnacanthal. These derivatives share a similar structure as follows:

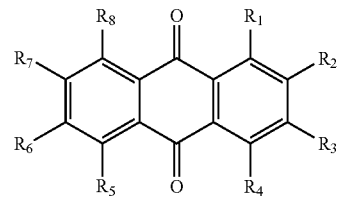

Where R1, R2, R3, R4, R5, R6, R7 and R8 are hydrogen, hydroxyl, hydroxylalkyl, halogen, carboxyl, alkyl, alkyoxyl, alkenyl, alkenyloxyl, alkynyl, alkynyloxyl, heterocyclyl, aromatic, or aryl group, sugars such as glucose.

In a particular embodiment, the invention is directed to anthraquinone derivatives that are contained in extracts derived from plant families including but not limited to Polygonaceae, Rhamnaceae, Fabaceae, Asphodelaceae, and Rubiaceae so on. These compounds can be from any part of plants such as leaf, stem, bark, root and fruits. Plant materials can be wet and dry, but preferably dry plant materials. To meet the biochemical agricultural products, solvents and processes that are used in the extraction and purification must meet the requirements of National Organic Program (NOP) [http://www.ams.usda.gov/AMSv1.0/nop,].

In a more particular embodiment, the plant extract is derived from a member of the Polygonaceae family. As defined herein, "derived from" means directly isolated or obtained from a particular source or alternatively having identifying characteristics of a substance or organism isolated or obtained from a particular source. In a particular embodiment, extract in said combination contains at anthraquinone derivatives physcion and optionally emodin. Members of the Polygonaceae family include but are not limited to *Acetosella, Antigonon, Aristocapsa, Bilderdykia, Brunnichia, Centrostegia, Chorizanthe, Coccoloba, Coccolobis, Coccolobo, Corculum, Dedeckera, Delopyrum, Dentoceras, Dodecahema, Emex, Eriogonum, Fafopyrum, Fagopyrum, Fallopia, Gilmania, Goodmania, Harfordia, Hollisteria, Koenigia, Lastarriaea, Mucronea, Muehlenbeckia, Nemacaulis, Oxyria, Oxytheca, Perscarioa, Persicaria, Pleuropterus, Podopterus, Polygonella, Polygonum, Pterostegia, Rheum, Rumex, Ruprechtia, Stenogonum, Systenotheca, Thysanella, Tovara, Tracaulon, Triplaris* and even more particular embodiment, the extract may be derived from a *Reynoutria* (alternately referred to as *Fallopia*) sp. or *Rheum* species. In a most particular embodiment, the extract is derived from *Reynoutria sachalinensis*.

Anti-Phytopathogenic Agents

The formulated extract (such as products marketed under trade names REGALIA® and MILSANA®) can then be used in combination with other anti-phytopathogenic agents plant extracts, biopesticides, inorganic crop protectants (such as copper), surfactants (such as rhamnolipids; Gandhi et al., 2007) or natural oils such as paraffinic oil and tea tree oil possessing pesticidal properties or chemical fungicides or bactericides with either single site, multisite or unknown mode of action. As defined herein, an "anti-phytopathogenic agent" is an agent which modulates the growth of a plant pathogen on a plant or alternatively prevents infection of a plant by a plant pathogen. A plant pathogen includes but is not limited to a fungus, bacteria, virus, insects, nematodes and/or mollusca.

In a particular embodiment, the anti-phytopathogenic agent is a biopesticide alternatively referred to as a biocontrol agent. This biocontrol agent is in a more particular embodiment a non-*Bacillus*, non-*Pseudomonas*, non-*Brevabacillus*, non-*Lecanicillium*, non-*Ampelomyces*, non-*Phoma*, non-*Pseudozyma* biological control agent is an agent derived from *Streptomyces* sp., *Burkholderia* sp., *Trichoderma* sp., *Gliocladium* sp. Alternatively, the agent is a natural oil or oil-product having fungicidal and/or insecticidal activity (e.g., paraffinic oil, tea tree oil, lemongrass oil, clove oil, cinnamon oil, citrus oil, rosemary oil).

As noted above, the anti-phytopathogenic agent may be a single site anti-fungal agent which may include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine). In a more particular embodiment, the antifungal agent is a demethylation inhibitor selected from the group consisting of imidazole (e.g., triflumizole), piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole, propiconazole). In a most particular embodiment, the antifungal agent is myclobutanil. In yet another particular embodiment, the antifungal agent is a quinone outside inhibitor (e.g., strobulurin). The strobulurin may include but is not limited to azoxystrobin, kresoxim-methoyl or trifloxystrobin. In yet another particular embodiment, the anti-fungal agent is a quinone, e.g., quinoxyfen (5,7-dichloro-4-quinolyl 4-fluorophenyl ether).

In yet a further embodiment, the antimicrobial agent is a multi-site non-inorganic, chemical fungicide selected from the group consisting of a nitrile (e.g., chloronitrile or fludioxonil), quinoxaline, sulphamide, phosphonate, phosphite, dithiocarbamate, chloralkylhios, phenylpyridin-amine, cyano-acetamide oxime.

In yet another embodiment, the anti-phytopathogenic agent is an anti-bacterial agent. This anti-bacterial agent includes but is not limited to carbamates, organophosphates, cyclodiene organochlorides, phenylpyrazoles, pyrethroids, pyrethrins, neonicotinoids, nitroguanadines, nicotine, Spinosyn, glycosides, juvenile hormone analogues and other insect growth regulators, pyridine azomethine, pyridine carboxamide, tetrazine, thiazolidinone, 2,4-diphenyloxzoline derivatives, organotin, pyrrole, buprofezin, hydramethylnon, naphtoquinon derivatives, pyridazinone, phenoxypyrazole, tetronic acid, carbazate, rotenone, organochlorine-diphenylaliphatics.

Uses

The said plant extract or formulated product can be used simultaneously with the other component or components in a tank mix or in a program (sequential application called rotation) with predetermined order and application interval during the growing season. When used in a combination with the above-mentioned pesticidal products, at concentration lower than recommended in the product label, the combined efficacy of the two or more products (one of which is the said plant extract) is in a preferred embodiment, higher than each individual component's effect added together. Hence, the pesticidal effect is enhanced by synergism between these two (or more) products, and the risk for the development of pesticide resistance among the plant pathogenic strains is reduced.

Target plants to be protected within the scope of the present invention comprise, for example, the following species of plants: cereals (wheat, barley, rye, oats, rice, sorghum and related crops), beet (sugar beet and fodder beet), pommes and soft fruit (apples, pears, plum, peaches, almonds, cherries, strawberries, raspberries and blackberries), leguminous plants (beans, lentils, peas and soybeans), oil plants (rape, mustard, poppy, olives, sunflowers, coconuts, castor oil plants, cocoa beans and ground nuts), cucurbits (cucumber, melons, pumpkins, eggplant), fiber plants (cotton, flax, hemp and jute), citrus fruit (oranges, lemon, grapefruits and mandarins), vegetables (spinach, lettuce, asparagus, cabbages, carrots, onions, tomatoes, potatoes and paprika), lauraceae (avocadoes, cinnamon and camphor) or plants such as maze, tobacco, nuts, coffee, sugar cane, tea, vines, hops, bananas and natural rubber plants, as well as ornamentals (composites), areas of grass or general low cover crops which counteract erosion or desiccation of the soil and are useful in cultures of trees and perennials (fruit plantations, hop plantations, maze fields, vineyards, etc.).

The preferred method of applying combinations of products in the present invention is a foliar application (spraying, atomizing, dusting, scattering or pouring) with or without a carrier. The number of applications and the rate of application depend on the risk of infestation by a pathogen. For example, the foliar pesticidal treatments with combinations and mixtures covered in this patent can be made once in every 7 to 14 days at 25 to 10.000-fold lower rates than recommended in the product label. Product mixtures and combinations targeted in the present invention may also be applied to seeds by impregnating the seeds either with a liquid formulation containing the active ingredient or coating them with a solid formulation. In special cases, further types of application are also possible. These include soil drench or selective treatment of plant stems or buds.

The mixtures of the present invention and, where appropriate, a solid or liquid adjuvant are prepared in known manner. For example, the mixtures may be prepared by homogeneously mixing and/or grinding the active ingredients with extenders such as solvents, solid carriers and, where appropriate, surface-active compounds (surfactants). The compositions may also contain further ingredients such as stabilizers, viscosity regulators, binders, adjuvants as well as fertilizers or other active ingredients in order to obtain special effects.

EXAMPLES

As will be set forth below, in satisfaction of the foregoing objects and advantages, examples of methods for increasing the efficacy of two or more products by using them at rates that produce synergistic or additive effects. The compositions and methods described here have been proven effective in reducing the disease incidence and severity in greenhouse-grown cucumbers (*Cucumis sativus*) but the concept can be used effectively for other plant varieties and species. The compositions and methods are particularly effective against cucumber powdery mildew but they can be applied to other fungal, bacterial, and viral plant diseases as well such as grey mold, leaf spots, bacterial wilt, scab, anthracnose, tobacco mosaic virus etc.

Materials and Methods

Powdery Mildew

Examples I-V and X-XI

The studies were conducted in a green house. Experimental design of the studies for synergism followed the Burpee and Latin (2008). Powdery mildew, caused by *Sphaerotheca fuliginea*, was used for investigating the efficacy of the treatments.

Cucumber seeds cv. "SMR 58" (Irwin & Sons Ag Supply, Inc. Cheshire, Oreg.) were grown in plastic 4-inch pots with potting soil mix (Rod McLellan Company, Marysville, Ohio). The plants were treated at 2-true leaf stage. The compounds at various rates were sprayed with a 2-oz mist sprayer at 2 ml per plant at upper side and 1 ml at lower side of the leaves. The treated plants were left for 3-4 hours under florescent light to dry before inoculation.

A conidia suspension of *Sphaerotheca fuliginea*, the causal agent of powdery mildew disease on cucumber, was prepared by cutting diseases leaves of the cucumber plants that are served for conservation of inoculum. The suspension were adjusted to $2.0 \times 10^5$ conidia per ml and applied with a 2-oz mist sprayer at 2 ml per plant on the upper side of the leaves. The inoculated plants were placed in a greenhouse and the treatments were arranged in randomized complete blocks with 4 to 6 replicates at 25° C. to 30° C.

The disease severity (percentage area covered with colonies) of the first leaves were rated according to James (1971). Disease severity and percentage control were analyzed with analysis of variance (ANOVA) and means of the treatments were compared with Fisher's Protected Least Difference (LSD) at p=0.05 level. Synergetic effect was calculated and analyzed with Limpel's formula (Limpel et al., 1962; Richer, 1987).

Lettuce Downy Mildew

Examples VI-VII

Synergy between MBI-106 and acibenzolar-S-methyl or mefenoxam which control a specific class of pathogens Oomycetes was tested with lettuce downy mildew following Su et al. (2004).

To prepare inoculum of downy mildew, lettuce seeds were placed on 5-mm petri-dishes with about 20-30 seeds in each and watered with sterile water, then supplied with ½ strength of Hoagland's solution after germination. The petri dishes were placed at 20° C. growth chamber for 7-10 days. The spores of *Bremia lactucae* was inoculated on lettuce cotyledons and cultured for 7-10 days at 15° C. for sporulation to occur. Cotyledons with sporulation were cut off and placed in a falcon tube with sterile water. The cotyledons were vortexed for 15 seconds three times and filtered through a 100-uμm mesh to collect sporangia. The solution was adjusted to 0.5 to $1.0 \times 10^5$ spores/ml for inoculation.

Four test plants were seeded in each 2-in pots and then placed at 20° C. for 7-10 days to grow cotyledons. Plants were ready for test when the first true leaf was emerging.

The lettuce plants were treated with the materials and left to dry or overnight. Then the plants were inoculated with sporangial solution. The treatments were arranged in a randomized complete block design with four replicates. The inoculated plants were placed in darkness in growth chamber for 48 hours and then incubated under 12-h light period at 15° C. Eight to ten days after inoculation, the cotyledons were rated for disease severity (percentage area covered with sporangiophores).

Seed Treatment

Examples VIII-IX

The experiments described below were conducted with soybean but similar procedures are used with other crops such as cereals, corn, cotton, and potatoes.

The experiments were conducted in a greenhouse following the procedure developed by Hwang et al. (2006). The isolate of *Rhizoctonia solani* was grown on potato dextrose agar plates and cultured for 5 days for inoculating oat or wheat grain. One liter of grain was soaked overnight at room temperature (25° C.) and rinsed three times with tape water. The 8×12-in autoclave bags were filled with the grain up to ⅓ full were autoclaved at 121° C. for 15 min. The autoclaved grain then was then inoculated with 5 pieces of 1×1 cm plug of the 5-day culture of *R. solani* per bag and cultured for 5 days at room temperature (25° C.). The bags were left open in laminar flow hood to let the grain completely dry.

The blank seed sample of 10 g to be coated was placed in a flask. Coating agent SEPIRET® 1171-O (Becker Underwood Ltd., Ames, Iowa) was put into the flasks together with the compound of interest, and the flask was shaken vigorously so that the seed picked up the compound. The procedure was repeated with fresh seed sample of cvs. "White Lion" (Kitazawa Seed Co., Oakland, Calif.) or "Viking 2265" (Johnny's Selected Seeds, Winslow, Me.) in the same flask for the treatments. After the seeds were coated, they were left to air dry before planting.

To prepare the soil, five hundred milliliters of the dried grains with inoculum were blended for 15 seconds three times and the powder was mixed with sterile sand at 1:1 (v/v) to dilute the inoculum. The sand mix was further used to prepare soil mix at various proportions 1:350 to 1:800 (inoculum:soil) for soybean to generate various disease levels in repeated tests.

The coated seeds were planted in the pots with infested soil. There were three replicates of each treatment which were arranged in a complete randomized block design and placed at 25 to 30° C. in a greenhouse.

After 10 to 20 days, depending on disease pressure and temperature, emergence of each treatment was rated and compared. Biomass was measured by weighing the aboveground portion which was measured for each replicate of the plant material.

Example I

Synergistic Effect Between Formulated *R. sachalinensis* Extract and Myclobutanil (Test I)

MBI-106 (formulated *R. sachalinensis* extract marketed as REGALIA® SC by Marrone Bio Innovations, Inc., Davis, Calif.) diluted at 10-fold lower than label rates of 1500× and 2000× and myclobutanil (formulated as RALLY® 40W, Dow AgroSciences LLC, Indianapolis, Ind.) at concentrations of 0.25 ug/ml, 0.1 ug/ml, and 0.05 ug/ml (450 to 2.250-fold lower than recommended label rates) were applied alone or in tank mix.

Disease severity was significantly reduced in MBI-106 at 1500× and 2000× in combination with myclobutanil at 0.25 ug/ml than that when they were used alone (Table 1). Significant increase in control efficacy was found with the combination of MBI-106 2000× tank mixed with myclobutanil at rates of 0.25 ug/ml and 0.05 ug/ml (Table 2).

Example II

Synergistic Effect Between *R. sachalinensis* Extract and Myclobutanil (Test II)

In a second test using MBI-106 (formulated as REGALIA® SC) and myclobutanil (formulated as RALLY® 40W), higher efficacy was found when MBI-106 at 2000× (10-fold lower than label rate) dilution in combination with myclobutanil at rates of 0.25, 0.1, and 0.05 ug/ml, and when MBI-106 at 1500× was tanked mixed with myclobutanil at 0.05 ug/ml (Table 3). Significant synergistic effect was displayed when MBI-106 diluted at 1500× and 2000× was combined with myclobutanil at the lowest rate of 0.05 ug/ml (Table 4).

Example III

Synergistic Effect Between Formulated *R. sachalinensis* Extract and Quinoxyfen

MBI-106 diluted at 1500× or 2000× was applied alone or in combination with quinoxyfen (formulated as QUINTEC®, Dow AgroSciences LLC, Indianapolis, Ind.) at 0.05 and 0.01 ug/ml (2,000 to 10.000-fold lower than label rates) either alone or in a tank mix. The results are shown in Tables 5 and 6. The most significant synergistic effect and enhanced disease control was found at *R. sachalinensis* product dilution of 2000× with quinoxyfen at 0.01 ug/mL. Quinoxyfen has a new multi-site mode of action affecting G-proteins in early cell signaling.

Example IV

Synergistic Effect Between Formulated *R. sachalinensis* Extract and Azoxystrobin MBI-106 diluted at 1500× or 2000× was applied alone or in combination with azoxystrobin (formulated as QUADRIS®, Syngenta Corporation, Wilmington, Del.) at a rate 0.25, 0.5, 1.0, 5.0, and 10 ug/mL (25 to 1020-fold lower than recommended label rates) either alone or in a tank mix. The results are shown in Tables 7 and 8. Of all tested combinations, mixes with *R. sachalinensis* extract at 2000× dilution and azoxystrobin at either 5.0 or 0.5 ug/mL provided the greatest synergy, and the fungicidal efficacy was significantly greater than expected compared to the single-compound use data.

Example V

Synergistic Effect Between Formulated *R. sachalinensis* Extract and Triflumizole MBI-106 (formulated *R. sachalinensis* extract marketed as REGALIA® SC by Marrone Bio Innovations, Inc., Davis, Calif.) at 2500× dilution (10-fold lower than label rate) and triflumizole (formulated as PROCURE® 480SC, Chemtura Corporation, Middlebury, Conn.) at concentrations of 1.0 ug/ml, 0.5 ug/ml, and 0.25 ug/ml (150 to 600-fold lower than recommended label rates) were applied alone or in tank mix to.

Disease severity was significantly reduced (P<0.0001) in treatments sprayed with MBI-106 at 2500× dilution in combination with triflumizole compared with a treatment where MBI-106 was used alone (Table 9). Synergistic effect in efficacy was found at the combination of MBI-106 2500× tank mixed with triflumizole at rates of 1.0 ug/ml, 0.5 ug/ml, and 0.25 ug/ml (Table 10).

Example VI

Synergistic Effect Between *R. sachalinensis* Extract and Acibenzolar-S-Methyl in Controlling Lettuce Downy Mildew MBI-106 (formulated *R. sachalinensis* extract marketed as REGALIA® SC by Marrone Bio Innovations, Inc., Davis, Calif.) was used alone at 200× dilution or in combination with acibenzolar-S-methyl (formulated as ACTIGARD®, Syngenta Crop Protection, Inc., Greensboro, N.C.) at concentrations of 25 ug/ml to control lettuce downy mildew.

Disease severity was significantly reduced (p=0.0004) in MBI-106 at 200× dilution in combination with acibenzolar-S-methyl compared to treatments in which they were used alone (Table 11). There is a synergistic effect in efficacy in the tank mix of MBI-106 200× and acibenzolar-S-methyl (Table 12).

Example VII

Synergistic Effect Between *R. sachalinensis* Extract and Mefenoxam in Controlling Lettuce Downy Mildew To investigate the synergistic effect of *Reynoutria* and MBI-106, formulated product REGALIA® ME by Marrone Bio Innovations, Inc., Davis, Calif. was used at 400× dilution rate in combination with mefenoxam (formulated as RIDOMIL GOLD®, Syngenta Crop Protection, Inc., Greensboro, N.C.) at concentrations of 37.5 µg/ml, 75.0 µg/ml, and 150 µg/ml to control lettuce downy mildew.

Disease severity was significantly reduced (p<0.0001) in MBI-106 at 400× dilution in combination with mefenoxam compared to treatments in which they were used alone at each concentration (Table 13). Synergistic effect in efficacy of the tank mix of MBI-106 200× and mefenoxam was found in combinations of MBI-106 and each concentration of mefenoxam (Table 14).

Example VIII

*R. sachalinensis* Extract as a Seed Treatment Agent and its Synergy with Azoxystrobin in Controlling *Rhizoctonia solani*

*Reynoutria sachalinensis* was extracted with ethanol at 5% (w/w) and used for seed coating at 0.2117 g/kg seed, either alone or in combination with azoxystrobin (QUADRIS®, Syngenta Crop Protection, Inc., Greensboro, N.C.) at 0.0298 g/kg seed to control *Rhizoctonia solani* on soybean. The emergence rate was higher in the inoculated seeds treated with MBI-106 compared to the inoculated untreated control, and when used in combination with azoxystrobin, the emergence rate was higher than when either product was used alone (Table 15). A synergistic effect was found when both materials were used in combination (Table 16).

Example IX

*R. sachalinensis* Extract as a Seed Treatment Agent and Synergy with Fludioxonil in Controlling *Rhizoctonia solani*

The ethanol extract of *R. sachalinensis* was also used at the rates of 0.03175 g/kg seed and 0.635 g/kg seed for seed coating, either alone or in combination with fludioxonil (formulated as Scholar® by Syngenta Crop Protection, Inc., Greensboro, N.C.) to control *Rhizoctonia solani* on soybean. The emergence rates and biomass were higher in the MBI-106 treated seeds compared to the inoculated untreated control and also higher when used in combination with fludioxonil at the rate of 0.0596 g/kg seed (Table 17). Synergistic effect was found in the two rates of MBI-106 when used in combination with fludioxonil (Table 18).

Example X

Synergistic Effect Between Formulated *R. sachalinensis* Extract and Propiconazole in Controlling Cucumber Powdery Mildew MBI-106 (formulated *R. sachalinensis* extract marketed as REGALIA® ME by Marrone Bio Innovations, Inc., Davis, Calif.) at 2500× dilution and propiconazole (formulated as PROPIMAX® EC, Dow AgroSciences LLC, Indianapolis, Ind.) at concentrations of 1.0 ug/ml were applied alone or in tank mix.

Disease severity was significantly reduced (P<0.0001) in treatments sprayed with MBI-106 at 2500× dilution in combination with propiconazole (Table 19). There is a synergistic effect in control efficacy in the combination of MBI-106 2500× tank mixed with propiconazole (Table 20).

Example XI

Synergistic Effect Between *R. sachalinensis* Extract and Quinoxifen (Test II) in Controlling Cucumber Powdery Mildew MBI-106 (formulated *R. sachalinensis* extract marketed as REGALIA® SC by Marrone Bio Innovations, Inc., Davis, Calif.) was used alone at 2000× dilution or in combination with azoxystrobin at three concentration 0.5, 0.25, and 0.1 ug/ml to control cucumber powdery mildew.

The control efficacy in MBI-106 at 2000× dilution in combination with azoxystrobin treatments are higher that they are used alone (Table 21). Synergistic effect in control efficacy of the tank mix of MBI-106 2000× exists in combinations of MBI-106 and each concentration of azoxystrobin (Table 22).

Tables

TABLE 1

Disease severity and percentage control of MBI-106 and myclobutanil (RALLY® 40W) when used alone or in tank mix.[1]

| Treatment | Dilution/Rate | Severity (%)[z] | Control (%) |
|---|---|---|---|
| Untreated control | N/A | 98.3 a | 0.0 e |
| myclobutanil | 0.25 ug/ml | 16.7 cd | 83.1 bc |
| myclobutanil | 0.1 ug/ml | 95.0 a | 3.2 e |
| myclobutanil | 0.05 ug/ml | 95.8 a | 2.5 e |
| Reynoutria extract | 1500× | 15.8 cd | 84.0 bc |
| Reynoutria extract | 2000× | 35.8 b | 63.5 d |
| Reynoutria extract + myclobutanil | 1500× 0.25 ug/ml | 1.2 e | 98.8 a |
| Reynoutria extract + myclobutanil | 2000× 0.25 ug/ml | 0.2 e | 99.8 a |
| Reynoutria extract + myclobutanil | 1500× 0.1 ug/ml | 11.8 de | 87.9 ab |
| Reynoutria extract + myclobutanil | 2000× 0.1 ug/ml | 27.5 bc | 72.2 dc |
| Reynoutria extract + myclobutanil | 1500× 0.05 ug/ml | 17.5 cd | 82.4 bc |
| Reynoutria extract + myclobutanil | 2000× 0.05 ug/ml | 20.8 cd | 79.0 bc |
|  |  | P < 0.0001 | P < 0.0001 |

[1]Data in Column 3 (Severity (%)) are means of six replicates. Means with the same letter in a column are not significantly different according to Fisher's Protected Least Significant Difference (LSD) at P = 0.05 level.

TABLE 2

Expected efficacy (Ee)[2] of each product combination, and the statistical significance of detected synergism between MBI-106 (REGALIA® SC) and myclobutanil (RALLY® 40W)

| Treatment | Dilution/Rate | Control (%) | $E_e$[3] | T-test |
|---|---|---|---|---|
| Reynoutria extract + myclobutanil | 1500× 0.25 ug/ml | 98.8 | 97.3 | n.s. |
| Reynoutria extract + myclobutanil | 2000× 0.25 ug/ml | 99.8 | 93.8 | *** |
| Reynoutria extract + myclobutanil | 1500× 0.1 ug/ml | 87.9 | 84.5 | n.s. |
| Reynoutria extract + myclobutanil | 2000× 0.1 ug/ml | 72.2 | 64.7 | n.s.[4] |
| Reynoutria extract + myclobutanil | 1500× 0.05 ug/ml | 82.4 | 84.4 | n.s. |
| Reynoutria extract + myclobutanil | 2000× 0.05 ug/ml | 79.0 | 64.4 | *[5] |

[2]$E_e$ is the Expected efficacy and is determined with the Limpel's formula $E_e = X + Y - (XY)/100$ (Limpel et al., 1962; Richer, 1987).
[3]Data are means of six replicates. Means with the same letter in a column are not significantly different according to Fisher's Protected Least Significant Difference (LSD) at P = 0.05 level.
[4]n.s.: Not significant
[5]* and ***: Significant at P < 0.05 and 0.001 respectively.

TABLE 3

Disease severity and percentage control of MBI-106 (REGALIA® SC) and myclobutanil (RALLY® 40W) when used alone or in tank mix in a repeated test.

| Treatment | Dilution/Rate | Severity (%)[z,6] | Control (%) |
|---|---|---|---|
| Untreated control | N/A | 91.3 a | 0.0 e |
| myclobutanil | 0.25 ug/ml | 53.8 bcd | 41.3 dc |
| myclobutanil | 0.1 ug/ml | 80.0 ab | 12.2 de |
| myclobutanil | 0.05 ug/ml | 93.8 a | -2.8 e |
| Reynoutria extract | 1500× | 20.0 ef | 77.9 ab |
| Reynoutria extract | 2000× | 63.8 abc | 29.8 cde |
| Reynoutria extract + myclobutanil | 1500× 0.25 ug/ml | 46.3 cde | 48.8 bc |
| Reynoutria extract + myclobutanil | 2000× 0.25 ug/ml | 33.8 cdef | 62.7 bc |
| Reynoutria extract + myclobutanil | 1500× 0.1 ug/ml | 33.8 cdef | 62.6 bc |
| Reynoutria extract + myclobutanil | 2000× 0.1 ug/ml | 38.8 cde | 57.3 bc |
| Reynoutria extract + myclobutanil | 1500× 0.05 ug/ml | 1.8 f | 98.1 a |
| Reynoutria extract + myclobutanil | 2000× 0.05 ug/ml | 21.3 def | 77.0 ab |
|  |  | P < 0.0001 | P < 0.0001 |

[6]Data are means of four replicates. Means with the same letter in a column are not significantly different according to Fisher's Protected Least Significant Difference (LSD) at P = 0.05 level.

TABLE 4

Synergistic effect between MBI-106 (REGALIA® SC) and myclobutanil (RALLY® 40W) in a repeated test.

| Treatment | Dilution/Rate | Control (%) | $E_e$[z] | T test |
|---|---|---|---|---|
| Reynoutria extract + myclobutanil | 1500× 0.25 ug/ml | 48.8 | 87.0 | n.s. |
| Reynoutria extract + myclobutanil | 2000× 0.25 ug/ml | 62.7 | 58.8 | n.s. |
| Reynoutria extract + myclobutanil | 1500× 0.1 ug/ml | 62.6 | 80.6 | n.s. |
| Reynoutria extract + myclobutanil | 2000× 0.1 ug/ml | 57.3 | 38.3 | n.s. |
| Reynoutria extract + myclobutanil | 1500× 0.05 ug/ml | 98.1 | 77.3 | *** |

TABLE 4-continued

Synergistic effect between MBI-106 (REGALIA ® SC) and myclobutanil (RALLY ® 40W) in a repeated test.

| Treatment | Dilution/Rate | Control (%) | $E_e^z$ | T test |
|---|---|---|---|---|
| Reynoutria extract + myclobutanil | 2000× 0.05 ug/ml | 77.0 | 27.8 | ** |

$^z E_e$ is the Expected efficacy and is determined with the Limpel's formula $E_e = X + Y - (XY)/100$ (Limpel et al., 1962; Richer, 1987).
 and *: Significant at P < 0.01 and 0.001 respectively.
n.s.: Not significant

TABLE 5

Disease severity and percentage control of MBI-106 (formulated R. sachalinensis extract) and quinoxyfen (QUINTEC ®) when used alone or in tank mix.

| Treatment | Dilution/Rate | Severity (%) | Control (%) |
|---|---|---|---|
| Untreated control | N/A | 91.3 a | 0 |
| Reynoutria extract | 1500× | 20.0 c | 77.93 |
| Reynoutria extract | 2000× | 63.8 b | 29.75 |
| quinoxyfen | 0.05 ug/ml | 30.0 c | 66.95 |
| quinoxyfen | 0.01 ug/ml | 90.0 a | 1.33 |
| Reynoutria extract + quinoxyfen | 1500× 0.05 ug/ml | 25.0 c | 72.65 |
| Reynoutria extract + quinoxyfen | 2000× 0.05 ug/ml | 12.5 c | 86.25 |
| Reynoutria extract + quinoxyfen | 1500× 0.01 ug/ml | 22.5 c | 75.28 |
| Reynoutria extract + quinoxyfen | 2000× 0.01 ug/ml | 13.8 c | 85.1 |
| n = 4, LSD | | P < 0.0001 | P < 0.0001 |

Data are means of four replicates. Means with the same letter in a column are not significantly different according to Fisher's Protected Least Significant Difference (LSD) at P = 0.05 level.

TABLE 6

Synergistic effect between MBI-106 (Reynoutria extract, REGALIA ® SC) and quinoxyfen (QUINTEC ®)

| Treatment | Dilution/Rate | Control (%) | $E_e$ | T-test |
|---|---|---|---|---|
| Reynoutria extract + quinoxyfen | 1500× 0.05 ug/ml | 72.65 | 92.7 | * |
| Reynoutria extract + quinoxyfen | 2000× 0.05 ug/ml | 86.25 | 76.8 | n.s. |
| Reynoutria extract + quinoxyfen | 1500× 0.01 ug/ml | 75.28 | 78.2 | n.s. |
| Reynoutria extract + quinoxyfen | 2000× 0.01 ug/ml | 85.1 | 30.7 | ** |

$^z E_e$ is the Expected efficacy and is determined with the Limpel's formula $E_e = X + Y - (XY)/100$ (Limpel et al., 1962; Richer, 1987).
* and **: Significant at P < 0.05 and 0.01 respectively.
n.s.: Not significant.

TABLE 7

Disease severity and percentage control of powdery mildew using MBI-106 (R. sachalinensis extract, REGALIA ® SC) and azoxystrobin (QUADRIS ®).

| Treatment | Dilution/Rate | Severity (%) | Control (%) |
|---|---|---|---|
| Untreated control | N/A | 92.5 a | 0.0 h |
| azoxystrobin | 10.0 ug/ml | 11.3 efg | 87.6 abc |
| azoxystrobin | 5.0 ug/ml | 5.3 fg | 94.3 ab |
| azoxystrobin | 1.0 ug/ml | 30.0 cdef | 68.1 bcdef |
| azoxystrobin | 0.5 ug/ml | 48.8 bc | 48.0 fg |
| azoxystrobin | 0.25 ug/ml | 45.0 bcd | 51.8 efg |

TABLE 7-continued

Disease severity and percentage control of powdery mildew using MBI-106 (R. sachalinensis extract, REGALIA ® SC) and azoxystrobin (QUADRIS ®).

| Treatment | Dilution/Rate | Severity (%) | Control (%) |
|---|---|---|---|
| Reynoutria extract | 1500× | 11.3 efg | 88.0 abc |
| Reynoutria extract | 2000× | 61.3 b | 34.3 g |
| Reynoutria extract | 2500× | 48.8 bc | 47.0 fg |
| Reynoutria extract + azoxystrobin | 1500× 10.0 ug/ml | 3.0 fg | 96.8 ab |
| Reynoutria extract + azoxystrobin | 2000× 10.0 ug/ml | 4.0 fg | 95.6 ab |
| Reynoutria extract + azoxystrobin | 2500× 10.0 ug/ml | 1.8 fg | 98.1 ab |
| Reynoutria extract + azoxystrobin | 1500× 5.0 ug/ml | 1.0 g | 98.9 ab |
| Reynoutria extract + azoxystrobin | 2000× 5.0 ug/ml | 0.8 g | 99.2 a |
| Reynoutria extract + azoxystrobin | 2500× 5.0 ug/ml | 2.0 fg | 97.9 ab |
| Reynoutria extract + azoxystrobin | 1500× 1.0 ug/ml | 11.3 efg | 87.6 abc |
| Reynoutria extract + azoxystrobin | 2000× 1.0 ug/ml | 12.5 efg | 86.3 abcd |
| Reynoutria extract + azoxystrobin | 2500× 1.0 ug/ml | 25.0 cdefg | 73.4 abcdef |
| Reynoutria extract + azoxystrobin | 1500× 0.5 ug/ml | 16.3 defg | 82.2 abcde |
| Reynoutria extract + azoxystrobin | 2000× 0.5 ug/ml | 11.3 efg | 87.7 abc |
| Reynoutria extract + azoxystrobin | 2500× 0.5 ug/ml | 43.8 bcd | 52.1 efg |
| Reynoutria extract + azoxystrobin | 1500× 0.25 ug/ml | 40.0 bcde | 56.4 defg |
| Reynoutria extract + azoxystrobin | 2000× 0.25 ug/ml | 25.0 cdefg | 73.0 abcdef |
| Reynoutria extract + azoxystrobin | 2500× 0.25 ug/ml | 36.3 bcde | 60.5 cdefg |
| N = 4 | | P < 0.0001 | P < 0.0001 |

TABLE 8

Synergistic effect between MBI-106 and azoxystrobin. Only treatments with statistically significant synergistic effect are included.

| Treatment | Rate/Dilution | Control (%) | $E_e$ | T-test |
|---|---|---|---|---|
| Reynoutria extract + azoxystrobin | 2000× 10.0 ug/ml | 95.6 | 91.9 | * |
| Reynoutria extract + azoxystrobin | 2500× 10.0 ug/ml | 98.1 | 93.4 | * |
| Reynoutria extract + azoxystrobin | 2000× 5.0 ug/ml | 99.2 | 96.3 | ** |
| Reynoutria extract + azoxystrobin | 2000× 0.5 ug/ml | 87.7 | 65.8 | ** |

TABLE 9

Disease severity and percentage control of R. sachalinensis and triflumizole (PROCURE ® 480SC) when used alone or in tank mix.

| Treatment | Dilution/Rate | Severity (%) | Control (%) |
|---|---|---|---|
| Untreated control | N/A | 97.5 a | 0.0 |
| Reynoutria extract | 2500× | 23.8 b | 75.6 |
| triflumizole | 1.0 ug/ml | 77.5 a | 20.5 |
| triflumizole | 0.5 ug/ml | 86.3 a | 11.5 |
| triflumizole | 0.25 ug/ml | 95.0 a | 2.6 |
| Reynoutria extract + triflumizole | 2500× 1.0 ug/ml | 6.3 b | 93.6 |

TABLE 9-continued

Disease severity and percentage control of R. sachalinensis and triflumizole (PROCURE ® 480SC) when used alone or in tank mix.

| Treatment | Dilution/Rate | Severity (%) | Control (%) |
|---|---|---|---|
| Reynoutria extract + triflumizole | 2500× 0.5 ug/ml | 15.0 b | 84.6 |
| Reynoutria extract + triflumizole | 2500× 0.25 ug/ml | 11.5 b | 88.2 |

Data in Column 3 (Severity (%)) are means of four replicates. Means with the same letter in a column are not significantly different according to Fisher's Protected Least Significant Difference (LSD) at P = 0.05 level.

TABLE 10

The expected efficacy ($E_e$) of each product combination, control efficacy (E), and the synergistic effect ($E/E_e > 1.0$) between MBI-106 (REGALIA ® SC) and triflumizole (PROCURE ® 480SC)

| Tank mix | Dilution/Rate | Control (%) | $E_e$ | $E/E_e$ |
|---|---|---|---|---|
| Reynoutria extract + triflumizole | 2500× 1.0 ug/ml | 93.6 | 80.6 | 1.2 |
| Reynoutria extract + triflumizole | 2500× 0.5 ug/ml | 84.6 | 78.4 | 1.1 |
| Reynoutria extract + triflumizole | 2500× 0.25 ug/ml | 88.2 | 76.2 | 1.2 |

$E_e$ is the expected efficacy and is determined with the Limpel's formula $E_e = X + Y - (XY)/100$ (Limpel et al., 1962; Richer, 1987).

TABLE 11

Disease severity and percentage control of MBI-106 (REGALIA ® SC) and acibenzolar-S-methyl (ACTIGARD ®) when used alone or in tank mix.

| Treatment | Dilution/Rate | Severity (%) | Control (%) |
|---|---|---|---|
| Untreated control | N/A | 90.0 a | 0.0 |
| acibenzolar-S-methyl | 25 ug/ml | 68.9 ab | 23.4 |
| Reynoutria extract | 200× | 57.0 b | 36.6 |
| Reynoutria extract + acibenzolar-S-methyl | 200× 25 ug/ml | 14.2 c | 84.2 |

TABLE 12

The expected efficacy ($E_e$) of each product combination, control efficacy (E), and the synergistic effect ($E/E_e > 1.0$) between MBI-106 (REGALIA ® SC) and acibenzolar-S-methyl (ACTIGARD ®).

| Tank mix | Control (%) | $E_e$ | $E/E_e$ |
|---|---|---|---|
| Reynoutria extract + acibenzolar-S-methyl | 84.2 | 51.5 | 1.6 |

TABLE 13

Disease severity and percentage control of MBI-106 (REGALIA ® ME) and mefenoxam (RIDOMIL GOLD ® SL)

| Treatment | Dilution/Rate | Severity (%) | Control (%) |
|---|---|---|---|
| Untreated control | N/A | 87.0 ab | 0.0 |
| mefenoxam | 150 ug/ml | 44.8 de | 48.5 |
| mefenoxam | 75 ug/ml | 54.2 cd | 37.7 |
| mefenoxam | 37.5 ug/ml | 89.3 a | −2.6 |
| Reynoutria extract | 400× | 68.0 bc | 21.8 |
| Reynoutria extract + mefenoxam | 400× 150 ug/ml | 14.5 f | 83.3 |
| Reynoutria extract + mefenoxam | 400× 75 ug/ml | 28.6 ef | 67.1 |
| Reynoutria extract + mefenoxam | 400× 37.5 ug/ml | 59.2 cd | 32.0 |

TABLE 14

The expected efficacy ($E_e$) of each product combination, actual control efficacy (E), and detected synergism ($E/E_e > 1.0$) between MBI-106 (REGALIA ® ME) and mefenoxam (RIDOMIL GOLD ® SL).

| Tank mix | Dilution/Rate | Control (%) | $E_e$ | $E/E_e$ |
|---|---|---|---|---|
| Reynoutria extract + mefenoxam | 400× 150 ug/ml | 83.3 | 59.7 | 1.4 |
| Reynoutria extract + mefenoxam | 400× 75 ug/ml | 67.1 | 51.3 | 1.3 |
| Reynoutria extract + mefenoxam | 400× 37.5 ug/ml | 32.0 | 19.7 | 1.6 |

TABLE 15

Emergence of soybean seedling and control of damping off by MBI-106 (ethanol extract) and azoxystrobin (QUADRIS ®).

| Treatment | Rate | Emergence (%) | Control (%) |
|---|---|---|---|
| Non-inoculated control | N/A | 90.1 a | N/A |
| Inoculated control | N/A | 4.9 c | 0.0 |
| Inoculated Reynoutria extract | 0.02117 g/kg | 11.1 c | 6.2 |
| Inoculated Reynoutria extract + azoxystrobin | 0.02117 g/kg 0.0298 g/kg | 92.6 a | 87.7 |
| Inoculated azoxystrobin | 0.0298 g/kg | 86.4 a | 81.5 |

TABLE 16

The expected efficacy ($E_e$) of each product combination, actual control efficacy (E), and detected synergism ($E/E_e > 1.0$) between MBI-106 (ethanol extract) and azoxystrobin (QUADRIS ®).

| Tank mix | Rate | Control (%) | $E_e$ | $E/E_e$ |
|---|---|---|---|---|
| Reynoutria extract + azoxystrobin | 0.02117 g/kg 0.0298 g/kg | 87.7 | 82.6 | 1.1 |

TABLE 17

Emergence of soybean seedlings and control of damping off by MBI-106 (Reynoutria ethanol extract) and fludioxonil (SCHOLAR ®).

| Treatment | Rate | Emergence (%) | Bio mass (g) | Control (%) |
|---|---|---|---|---|
| Inoculated control | N/A | 7.4 c | 0.8 c | 0.0 |
| Inoculated Reynoutria extract | 0.635 g/kg | 9.9 c | 1.4 c | 2.5 |
| Inoculated Reynoutria extract | 0.03175 g/kg | 16.0 c | 2.9 c | 8.6 |
| Inoculated Reynoutria extract + | 0.635 g/kg | 61.8 a | 17.0 a | 54.4 |

TABLE 17-continued

Emergence of soybean seedlings and control of damping off by MBI-106
(Reynoutria ethanol extract) and fludioxonil (SCHOLAR ®).

| Treatment | Rate | Emergence (%) | | Bio mass (g) | | Control (%) |
|---|---|---|---|---|---|---|
| fludioxonil | 0.0596 g ai/kg | | | | | |
| Inoculated | 0.03175 g/kg | 50.6 | a | 12.5 | b | 43.2 |
| Reynoutria extract + | | | | | | |
| fludioxonil | 0.0596 g ai/kg | | | | | |
| Inoculated fludioxonil | 0.0596 g ai/kg | 35.8 | b | 8.7 | b | 28.4 |

TABLE 18

The expected efficacy ($E_e$) of each product combination, actual
control efficacy (E), and detected synergism ($E/E_e > 1.0$) between
MBI-106 (ethanol extract) and fludioxonil (SCHOLAR ®).

| Tank mix | Rate | Control (%) | $E_e$ | $E/E_e$ |
|---|---|---|---|---|
| Inoculated Reynoutria extract + fludioxonil | 0.635 g/kg<br>0.0596 g ai/kg | 54.4 | 30.2 | 1.8 |
| Inoculated Reynoutria extract + fludioxonil | 0.03175 g/kg<br>0.0596 g ai/kg | 43.2 | 34.6 | 1.2 |

TABLE 19

Disease severity and percentage control of R. sachalinensis and
propiconazole (PROPIMAX ®) when used alone or in tank mix in
controlling cucumber powdery mildew.

| Treatment | Dilution/Rate | Severity (%) | Control (%) |
|---|---|---|---|
| Untreated control | N/A | 98.8 a | 0.0 |
| propiconazole | 1.0 ug/ml | 97.5 a | 1.3 |
| Reynoutria extract | 2500× | 61.3 b | 38.0 |
| Reynoutria + propiconazole | 2500×<br>1.0 ug/ml | 51.3 c | 48.1 |

TABLE 20

The expected efficacy ($E_e$) of each product combination,
control efficacy (E), and the synergistic effect
($E/E_e > 1.0$) between MBI-106
(REGALIA ® ME) and propiconazole (PROPIMAX ®).

| Tank mix | Dilution/Rate | control (%) | $E^e$ | $E/e_e$ |
|---|---|---|---|---|
| Reynoutria extract + propiconazole | 2500×<br>1.0 ug/ml | 48.1 | 38.8 | 1.2 |

TABLE 21

Disease severity and percentage control of R. sachalinensis and
azoxystrobin (QUADRIS ®) when used alone or in
tank mix in controlling cucumber powdery mildew.

| Treatment | Dilution/Rate | Severity % | Control (%) |
|---|---|---|---|
| Untreated control | N/A | 80.0 a | 13.5 |
| azoxystrobin | 0.5 ug/ml | 35.0 cd | 62.2 |
| azoxystrobin | 0.25 ug/ml | 80.0 a | 13.5 |
| azoxystrobin | 0.1 ug/ml | 72.5 abc | 21.6 |
| Reynoutria extract | 2000× | 75.0 ab | 18.9 |
| Reynoutria extract + azoxystrobin | 2000×<br>0.5 ug/ml | 11.3 d | 87.8 |
| Reynoutria extract + azoxystrobin | 2000×<br>0.25 ug/ml | 41.3 abcd | 55.4 |
| Reynoutria extract + azoxystrobin | 2000×<br>0.1 ug/ml | 36.5 bcd | 60.5 |

TABLE 22

The expected efficacy ($E_e$) of each product combination, control efficacy
(E), and the synergistic effect ($E/E_e > 1.0$) between MBI-106 (Regalia ®
SC) and azoxystrobin (Quadris ®) (Test II).

| Tank mix | Dilution/Rate | Control (%) | $E_e$ | $E/E_e$ |
|---|---|---|---|---|
| Reynoutria extract + azoxystrobin | 2000×<br>0.5 ug/ml | 87.8 | 69.3 | 1.3 |
| Reynoutria extract + azoxystrobin | 2000×<br>0.25 ug/ml | 55.4 | 29.9 | 1.9 |
| Reynoutria extract + azoxystrobin | 2000×<br>0.1 ug/ml | 60.5 | 36.4 | 1.7 |

LITERATURE CITED

Bardin, M., J. Fargues, et al. (2008). "Compatibility between biopesticides used to control grey mold, powdery mildew and whitefly on tomato." *Biological Control* 46: 476-483.

Bartlett, D. W., J. M. Clough, et al. (2002). "649-662." *Pest Management Science* 58: 649-662.

Belanger, R. R. and M. Benyagoub (1997). "Challenges and prospoects for integrated control of powdery mildews in the greenhouse." *Canadian Journal of Plant Pathology* 19: 310-314.

Bokshi, A. I., J. Jobling, et al. (2008). "A single application of Milsana followed by Bion assists in the control of powdery mildew in cucumber and helps overcome yield losses." *Journal of Horticultural Science and Biotechnology* 83: 701-706.

Braun, U., T. A. Cook, et al. (2002). The taxonomy of the powdery mildew fungi. *The powdery mildews: a comprehensive treatise*. R. R. Belanger, W. R. Bushnell, A. J. Dik and T. L. W. Carver. St. Paul, Minn., APS Press: 13-55.

Burpee, L. and R. Latin (2008). "Reassessment of fungicide synergism for control of dollar spot." *Plant Disease* 92: 601-606.

Daayf, F., A. Schmitt, et al. (1995). "The effects of plant extracts of *Reynoutria sachalinensis* on powdery mildew development and leaf physiology of long English cucumber." *Plant Disease* 79: 577-580.

De Waard, M. A. (1996). "Synergism and antagonism in fungicide mixtures containing sterol demethylation inhibitors." *Phytopathology* 86: 1280-1283.

Durrant, W. E. and X. Dong (2004). "Systemic acquired resistance." *Annual Review in Phytopathology* 42: 185-209.

Fraaije, B., J. A. Lucas, et al. (2003). *QoI resistance development in populations of cereal pathogens in the UK*. BCPC Internatrional Congress—Crop Science and Technology, Alton, Hants, UK, pp. 689-694.

Gandhi, N. R., V. P. Skebba, et al. (2007). Antimycotic rhamnolipid compositions and related methods of use, US patent application number 20070191292. USPTO. USA: 27 p.

Gisi, U. (1996). "Synergistic interactions of fungicides in mixtures" *Phytopathology* 86: 1273-1279.

Hafez, M. B., A. Schmitt, et al. (1999). "The side-effects of plant extracts and metabolites of *Reynoutria sachalinensis* (F. Schmidt) Nakai and conventional fungicides on the beneficial organism *Trichogramma cacoeciae* Marchal (Hym., Trichogrammatidae)." *Journal of Applied Entomology* 123: 363-368.

Holb, I. J. and G. Schnabel (2008). "The benefits of combining elemental sulfur with a DMI fungicide to control *Monilinia fructicola* isolates resistant to propiconazole." *Pest Management Science* 64: 156-164.

Horst, R. K., S. O. Kawamoto, et al. (1992). "Effect of sodium bicarbonate and oils on the control of powdery mildew and black spot on roses." *Plant Disease* 76: 247-251.

Hwang, S. F., H. Wang, et al. (2006). "Effect of seed treatment and root pathogens on seedling establishment and yield of alfalfa, birdfoot trefoil and sweetclover." *Plant Pathology Journal* 5:322-328.

James, W. C. (1971). *A manual assessment keys for plant diseases*. St. Paul, Minn., American Phytopathological Society.

Karaoglanidis, G. S, and D. A. Karadimos (2006). "Efficacy of strobilurins and mixtures with DM fungicides in controlling powdery mildew in field-grown sugar beet." *Crop Protection* 25: 977-983.

Konstantinidou-Doltsinis, S., E. Markellou, et al. (2007). "Control of powdery mildew of grape in Greece using Sporodex L and Milsana." *Journal of Plant Diseases and Protection* 114: 256-262.

Limpel, L. E., P. H. Schuldt, et al. (1962). N.E. Weed Control Conference.

May, R. M. (1985). "Evolution of pesticide resistance." *Nature* 315: 12-13.

McGrath, M. T. (2001). "Fungicide resistance in cucurbit powdery mildew: Experiences and challenges." *Plant Disease* 85: 236-245.

Reuveni, M. (2001). "Improved control of powdery mildew (*Sphaerotheca pannosa*) of nectarines in Israel using strobilurin and polyoxin B fungicides; mixtures with sulfur; and early bloom applications." *Crop Protection* 20: 663-668.

Richer, D. (1987). "Synergism—a patent view." *Pesticide Science* 19: 309-315.

Ross, A. F. (1961). "Systemic acquired resistance induced by localized virus infections in plants" *Virology* 14: 340-358.

Samoucha, Y. and Y. Cohen (1984). "Synergy between metalaxyl and macozeb in controlling downy mildew in cucumbers." *Phytopathology* 74: 1434-1437.

Schmitt, A. (2002). "Induced responses by plant extracts from *Reynoutria sachalinensis*: a case study." *Bull. IOBC/WPRS* 25: 83-89.

Schmitt, A., S. Kunz, et al. (2002). *Use of Reynoutria sachalinensis plant extracts, clay preparations and Brevibacillus brevis against funs al diseases of grape berries*. Fordergemeinschaft Okologisher Obstbau e.V. (FOKO) and der Staatlichen Lehr- und Versuchsanstalt fur Wein- und Obstbau (LvWO) Weinsberg. 10th International conference on cultication technique and phytopathological problems in organic fruit-growing and viticulture; presentations at the meeting from Feb. 4-7, 2002 Weinsberg, Germany, pp. 146-151.

Schmitt, A. and B. Seddon (2005). *Biocontrol of plant pathogens with microbial BCAs and plant extracts—advantages and disadvantages of single and combined use*. Modern fungicides and antifungal compounds IV. Proceedings of the 14th International Reinhardsbrunn Symposium 2004, BCPC, Atlon, UK, pp. 205-225.

Schnabel, G., B. K. Bryson, et al. (2004). "Reduced sensitivity in *Monilinia fructicola* to propiconazole in Georgia and implcations for disease management" *Plant Disease* 88: 1000-1004.

Su, H., A. H. C. van Bruggen, et al. (2004). "Sporulation of *Bremia lactucae* affected by temperature, relative humidity, and wind in controlled conditions". *Phytopathology* 94:396-401

Tuttle McGrath, M. (2003). "Occurrence of strobilurin resistance and impact on managing powdery mildew on cucurbits." *Cornell University; Vegetable MD Online* Retrieved Jul. 19, 2009, 2009, from http://vegetablemdonline.ppath.cornell.edu/NewsArticles/Cuc_Strob.htm.

Tuttle McGrath, M. (2006). "Guidelines for managing cucurbit powdery mildew in 2006." *Cornell University, Vegetable MD Online* Retrieved Jul. 19, 2009, 2009, from http://vegetablemdonline.ppath.cornell.edu/NewsArticles/Cuc_PM_2006.html.

Van den Bosch, F. and C. A. Gilligan (2008). "Models of fungicide resistance dynamics." *Annual Review in Phytopathology* 46: 123-147.

Vechet, L., L. Burketova, et al. (2009). "A comparative study of the efficiency of several sources of induced resistance to powdery mildew (*Blumeria graminis* f. sp. *tritici*) in wheat under field conditions." *Crop Protection* 28: 151-154.

Walters, D., D. Walsh, et al. (2005). "Induced resistance for plant disease control: maximizing the efficacy of resistance elicitors." *Phytopathology* 85: 1368-1373.

Wurms, K., C. Labbe, et al. (1999). "Effects of Milsana and Benzothiadiazole on the ultrastructure of powdery mildew haustoria in cucumber." *Phytopathology* 89: 728-736.

Wyenandt, C. A., M. T. McGrath, et al. (2009). "Fungicide resistance management guidelines for cucurbit downy and powdery mildew control in the mid-Atlantic and Northeast regions of the US." *Phytopathology* 99 (2009 APS Annual Meeting Abtsracts of Presentations): S144-S144.

What is claimed is:

1. A synergistic combination for use in modulation of a phytopathogenic infection comprising:
   (a) an extract derived from a *Reynoutria* sp. plant, wherein said extract comprises one or more anthraquinone derivatives that induce plant resistance to phytopathogens, wherein said derivative (i) has the structure

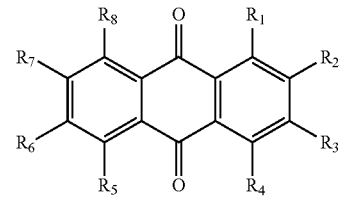

wherein R1, R2, R3, R4, R5, R6, R7 and R8 are hydrogen, hydroxyl, hydroxylalkyl, halogen, carboxyl, alkyl, or sugar; and
   (b) acibenzolar-S-methyl;
   wherein the amounts of the *Reynoutria* extract and acibenzolar-S-methyl in said combination provide for synergism of modulation of phytopathogenic infection, and wherein the synergism is measured by determining E/Ee and E/Ee is at least 1.2.

2. The synergistic combination of claim 1, wherein the combination is a composition.

3. The synergistic combination of claim 1, wherein the E/Ee is at least 1.6.

4. The synergistic combination of claim 1, wherein the phytopathogenic infection is a fungal infection.

5. The synergistic combination of claim 1, wherein the *Reynoutria* sp. is *Reynoutria sachalinensis*.

6. A method for modulating a phytopathogenic infection in a plant comprising applying to the plant and/or seeds thereof and/or substrate used for growing said plant an amount of the combination of claim 1 effective to modulate said phytopathogenic infection.

7. The method of claim 6, wherein the E/Ee is at least 1.6.

8. The method of claim 6, wherein the phytopathogenic infection is a fungal infection.

9. The method of claim 6, wherein the *Reynoutria* sp. is *Reynoutria sachalinensis*.

\* \* \* \* \*